(12) United States Patent
Yamanaka

(10) Patent No.: US 12,029,444 B2
(45) Date of Patent: Jul. 9, 2024

(54) GRIPPING MECHANISM

(71) Applicant: OLYMPUS CORPORATION, Tokyo (JP)

(72) Inventor: Noriaki Yamanaka, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 567 days.

(21) Appl. No.: 17/326,456

(22) Filed: May 21, 2021

(65) Prior Publication Data

US 2021/0282796 A1    Sep. 16, 2021

Related U.S. Application Data

(63) Continuation of application No. PCT/JP2018/044145, filed on Nov. 30, 2018.

(51) Int. Cl.
*A61B 17/29* (2006.01)
*B25B 7/08* (2006.01)

(52) U.S. Cl.
CPC .............. *A61B 17/29* (2013.01); *B25B 7/08* (2013.01); *A61B 2017/2936* (2013.01); *A61B 2017/2939* (2013.01); *A61B 2017/2947* (2013.01)

(58) Field of Classification Search
CPC .............. A61B 17/29; A61B 207/2939; A61B 207/2947; B25B 7/08
USPC .......................................................... 81/424
See application file for complete search history.

(56) References Cited

U.S. PATENT DOCUMENTS

| | | | | |
|---|---|---|---|---|
| 4,887,612 A | * | 12/1989 | Esser ................... | A61B 10/06 606/174 |
| 5,996,450 A | * | 12/1999 | St. John .................. | B25B 7/02 81/416 |
| 9,737,320 B2 | * | 8/2017 | Stopek ................... | A61B 17/29 |
| 9,844,388 B2 | * | 12/2017 | Ganter ................... | A61B 17/29 |
| 11,291,514 B2 | * | 4/2022 | Shuh ..................... | A61B 90/37 |
| 2014/0277106 A1 | | 9/2014 | Crews et al. | |
| 2017/0056098 A1 | | 3/2017 | Crews et al. | |

(Continued)

FOREIGN PATENT DOCUMENTS

| | | |
|---|---|---|
| JP | S48-031660 A | 4/1973 |
| JP | S49-041783 B1 | 11/1974 |
| JP | S59-093283 A | 5/1984 |

(Continued)

OTHER PUBLICATIONS

International Search Report dated Feb. 19, 2019 issued in PCT/JP2018/044145.

*Primary Examiner* — Hadi Shakeri
(74) *Attorney, Agent, or Firm* — Scully, Scott, Murphy & Presser, P.C.

(57) ABSTRACT

Provided is a gripping mechanism including: a frame; a first jaw that is supported by the frame so as to be rotatable about a first rotation axis; a second jaw that is supported by the frame so as to be rotatable about a second rotation axis that is different from the first rotation axis and that is parallel to the first rotation axis; a slit that is formed in at least one of the jaws; a transmission pin that passes inside the slit and that transmits a force between the jaws; and a wire that is connected to the first jaw and that transmits a rotational force about the first rotation axis to the first jaw through tension. Movement of the transmission pin inside the slit through rotation of the first jaw rotates the second jaw.

9 Claims, 13 Drawing Sheets

(56) References Cited

U.S. PATENT DOCUMENTS

2019/0059922 A1   2/2019  Yamanaka
2020/0397502 A1   12/2020 Crews et al.

FOREIGN PATENT DOCUMENTS

| JP | H01-101747 U | 7/1989 |
| JP | H04-013277 U | 2/1992 |
| JP | H11-347979 A | 12/1999 |
| JP | 2011-083476 A | 4/2011 |
| JP | 2016-518171 A | 6/2016 |
| WO | 2014151633 A1 | 9/2014 |
| WO | 2017/195246 A1 | 11/2017 |

* cited by examiner

GRIPPING MECHANISM

CROSS-REFERENCE TO RELATED APPLICATIONS

This is a continuation of International Application PCT/JP2018/044145 which is hereby incorporated by reference herein in its entirety.

TECHNICAL FIELD

The present invention relates to a gripping mechanism.

BACKGROUND ART

In the related art, there are known forceps in which a pair of jaws are opened and closed through pulling of two wires (for example, see PTL 1). In a case in which the pair of jaws are opened or closed by pushing a wire, a pushing force applied to the proximal end of the wire may not be transmitted to the distal end of the wire due to buckling or curvature of the wire. Such a disadvantage can be resolved when both opening and closing of the pair of jaws are performed by a pulling force of the wire. The forceps in PTL 1 have pulleys provided on the respective jaws, and a movable pulley is used to open and close the pair of jaws. Gears for linking the pair of jaws are provided on the pair of pulleys. Furthermore, the forceps in PTL 1 are of a both-opening type in which both jaws are rotated simultaneously. Forceps of the both-opening type have an advantage in that a large opening angle can be obtained.

CITATION LIST

Patent Literature

{PTL 1} Japanese Unexamined Patent Application, Publication No. 2011-83476

SUMMARY OF INVENTION

According to one aspect, the present invention provides a gripping mechanism including: a frame; a first jaw and a second jaw that are supported by the frame so as to be able to be opened and closed with respect to each other; a slit that is formed in at least one of the first jaw and the second jaw; a transmission pin that passes inside the slit and that transmits a force between the first jaw and the second jaw; and a wire that is connected to the first jaw, wherein a proximal-end section of the first jaw is supported by the frame so as to be rotatable about a first rotation axis, wherein a proximal-end section of the second jaw is supported by the frame so as to be rotatable about a second rotation axis that is different from the first rotation axis and that is parallel to the first rotation axis, wherein the wire gives a rotational force about the first rotation axis to the first jaw through tension, and wherein the transmission pin moves inside the slit through rotation of the first jaw about the first rotation axis, and the second jaw is rotated about the second rotation axis through the movement of the transmission pin inside the slit.

DESCRIPTION OF EMBODIMENT

A gripping mechanism according to one embodiment of the present invention will be described below with reference to the drawings.

Figure 1A:
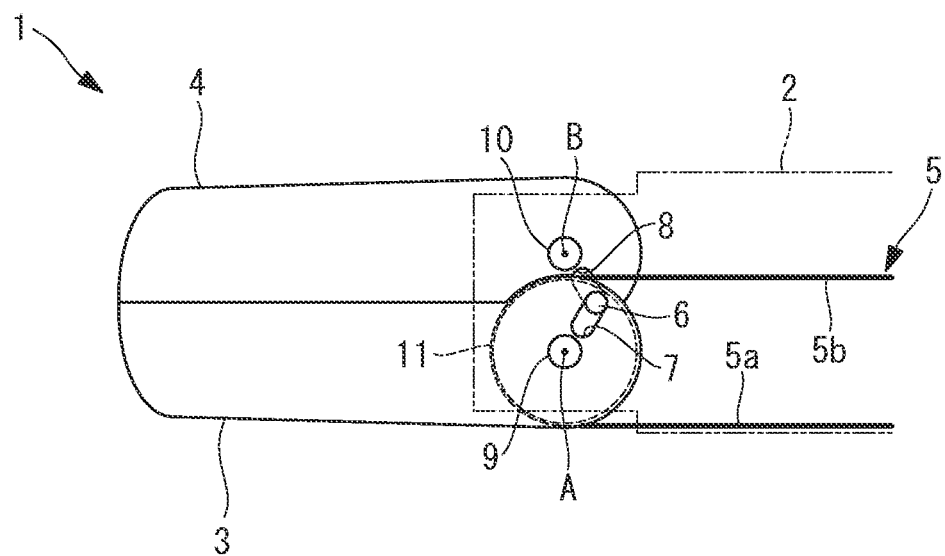
FIG. 1A is a schematic configuration view showing a closed state of a gripping mechanism according to one embodiment of the present invention.
Figure 1B:
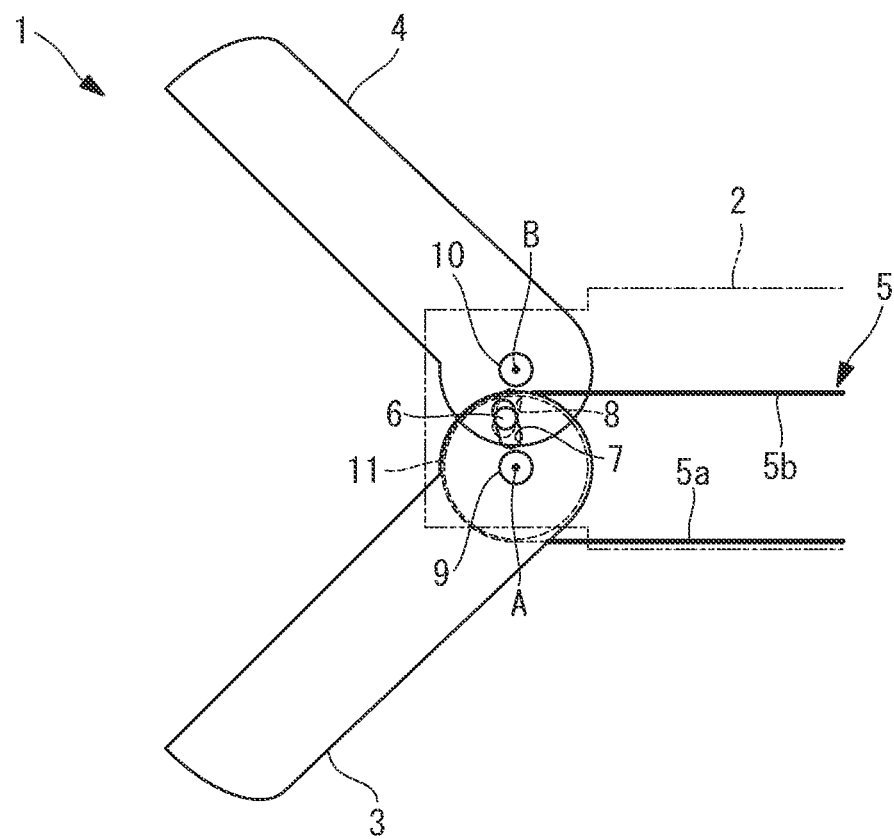
FIG. 1B is a schematic configuration view showing an open state of the gripping mechanism shown in FIG. 1A.

As shown in FIGS. 1A and 1B, a gripping mechanism 1 of this embodiment includes a frame 2, a pair of jaws 3 and 4 that are supported by the frame 2 so as to be able to be opened and closed with respect to each other, a wire 5 that is connected to the jaw 3 and that gives the jaw 3 a rotational force for opening and closing, and a transmission pin 6 that transmits the rotational force between the pair of jaws 3 and 4.

The frame 2 is an approximately tubular member.

The pair of jaws 3 and 4 are members each having a longitudinal direction and are disposed in parallel in a direction orthogonal to the central axis of the frame 2. In the following description, the direction of arrangement of the jaws 3 and 4 is defined as an up-down direction, and the direction perpendicular to the up-down direction and the central axis of the frame 2 is defined as a left-right direction. In the drawings to be referred to, the up-down direction of each figure corresponds to the up-down direction of the gripping mechanism 1, and the direction perpendicular to each figure corresponds to the left-right direction of the gripping mechanism 1. A distal-end section of the frame 2 covers left and right sides of proximal-end sections of the pair of jaws 3 and 4.

The first jaw 3, which is located at the lower side, is a driving jaw that is driven through pulling of the wire 5. The proximal-end section of the first jaw 3 is supported by the frame 2 so as to be rotatable about a first rotation axis A. Specifically, the proximal-end section of the first jaw 3 is connected by a connecting pin 9 to the distal-end section of the frame 2 so as to be rotatable about the first rotation axis A.

The second jaw 4, which is located at the upper side, is a driven jaw that follows the first jaw 3. The proximal-end section of the second jaw 4 is supported by the frame 2 so as to be rotatable about a second rotation axis B that is different from the first rotation axis A. Specifically, the proximal-end section of the second jaw 4 is connected by a connecting pin 10 to the distal-end section of the frame 2 so as to be rotatable about the second rotation axis B.

The first rotation axis A and the second rotation axis B are almost parallel to each other and extend in the left-right direction. Furthermore, the first rotation axis A and the second rotation axis B are arranged with a gap therebetween in the up-down direction.

Figure 2:
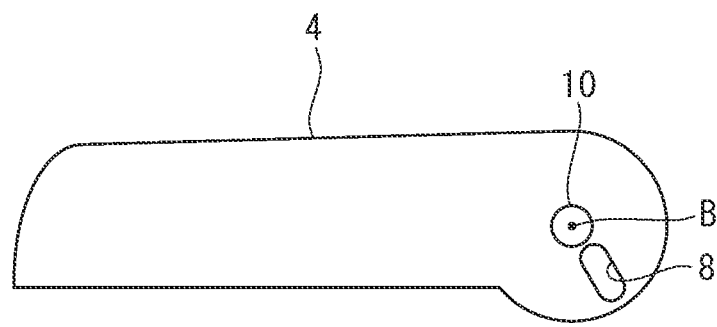
FIG. 2 is a schematic exploded view of an upper jaw, a lower jaw, and a transmission pin of the gripping mechanism shown in FIG. 1A.
Figure 2:
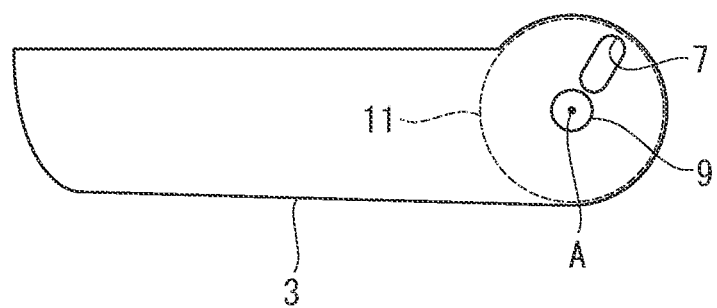

As shown in FIG. 2, a slit (first slit) 7 that penetrates the first jaw 3 in the left-right direction is formed in the proximal-end section of the first jaw 3, and a slit (second slit) 8 that penetrates the second jaw 4 in the left-right direction is formed in the proximal-end section of the second jaw 4. The slits 7 and 8 partially communicate with each other in the left-right direction, and the transmission pin 6 passes through the slits 7 and 8 in the left-right direction.

Figure 3:
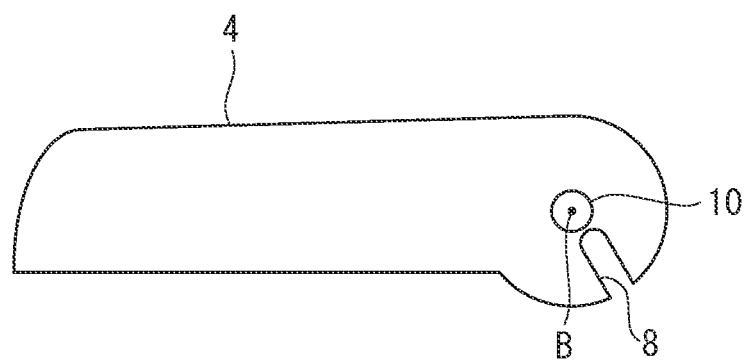
FIG. 3 is a schematic view of another example upper jaw of the gripping mechanism shown in FIG. 1A.

The slit 7 extends in a direction intersecting the circumferential direction around the first rotation axis A and is closed at both ends. The width of the slit 7 is slightly larger than the outer diameter of the transmission pin 6, whereby the transmission pin 6 can move inside the slit 7 in the longitudinal direction of the slit 7. The slit 8 extends in a direction intersecting the circumferential direction around the second rotation axis B and is closed at both ends. The width of the slit 8 is slightly larger than the outer diameter of the transmission pin 6, whereby the transmission pin 6 can move inside the slit 8 in the longitudinal direction of the slit 8. As shown in FIG. 3, the slit 8 may extend up to an outer circumferential surface of the second jaw 4, whereby one end of the slit 8 is open at the outer circumferential surface of the second jaw 4.

Through rotation of the first jaw 3 about the first rotation axis A, the transmission pin 6 moves in a front-back direction along the central axis of the frame 2 while moving inside the slit 7 in the longitudinal direction thereof. The moving transmission pin 6 gives the second jaw 4 a rotational force about the second rotation axis B, to rotate the second jaw 4 in the opposite direction from the first jaw 3.

In the example shown in the figure, the slits 7 and 8 are formed between the rotation axes A and B. The slit 7 is inclined in such a direction as to be gradually displaced downward from the proximal end toward the distal end, with respect to the longitudinal direction of the first jaw 3. The slit 8 is inclined in such a direction as to be gradually displaced upward from the proximal end toward the distal end, with respect to the longitudinal direction of the second jaw 4. In a closed state in which the longitudinal directions of the jaws 3 and 4 become parallel to the central axis of the frame 2, the proximal-end sections of the slits 7 and 8 communicate with each other, and the transmission pin 6 is disposed, inside the slits 7 and 8, at a position close to the proximal end.

A guide surface 11 for guiding the wire 5 is provided at the proximal-end section of the first jaw 3. The guide surface 11 is a circular or cylindrical surface centered on the first rotation axis A. The guide surface 11 is, for example, an outer circumferential surface of a pulley fixed to the proximal-end section of the first jaw 3. The wire 5 is wound over about half of the guide surface 11, and an intermediate position of the wire 5 is fixed to the guide surface 11. The wire 5 extends from the guide surface 11 toward the proximal end of the frame 2, and both ends of the wire 5 are disposed at positions close to the proximal end of the frame 2. Therefore, two wires 5a and 5b extend from the uppermost end and the lowermost end of the guide surface 11 toward the proximal end. Note that this wire may also be formed of a single wire instead of two wires.

When the wire 5a, which is located at the lower side of the first rotation axis A, is pulled, a tension is generated in the wire 5a, and a rotational force causing the first jaw 3 to swivel downward about the first rotation axis A is given to the first jaw 3 from the wire 5a. When the wire 5b, which is located at an upper side of the first rotation axis A, is pulled, a tension is generated in the wire 5b, and a rotational force causing the first jaw 3 to swivel upward about the first rotation axis A is given to the first jaw 3 from the wire 5b.

Next, the operation of the thus-configured gripping mechanism 1 will be described below.

The gripping mechanism 1 is mounted, as a gripping part, on a treatment tool for gripping living tissue etc. The treatment tool includes a long shaft and an operation part connected to a proximal end of the shaft, and the gripping mechanism 1 is connected to a distal end of the shaft. The wires 5a and 5b are guided to the operation part via the shaft.

When the wire 5a is pulled toward the proximal end through an operation of the operation part, a rotational force for rotating the first jaw 3 downward is transmitted from the wire 5a to the first jaw 3. Through the downward rotation of the first jaw 3, the transmission pin 6 moves inside the slits 7 and 8 toward the distal end (forward), and the moving transmission pin 6 transmits, to the second jaw 4, a rotational force for rotating the second jaw 4 upward, whereby the second jaw 4 is rotated upward. In this way, the pair of jaws 3 and 4 are simultaneously rotated in such directions as to be apart from each other, whereby the jaws 3 and 4 are opened.

On the other hand, when the wire 5b is pulled toward the proximal end through an operation of the operation part, a rotational force for rotating the first jaw 3 upward is transmitted from the wire 5b to the first jaw 3. Through the upward rotation of the first jaw 3, the transmission pin 6 moves inside the slits 7 and 8 toward the proximal end (backward), and the moving transmission pin 6 transmits, to the second jaw 4, a rotational force for rotating the second jaw 4 downward, whereby the second jaw 4 is rotated downward. In this way, the pair of jaws 3 and 4 are simultaneously rotated in such directions as to come close to each other, whereby the jaws 3 and 4 are closed. When the wire 5b is further pulled from the state in which the jaws 3 and 4 are closed, a gripping force is generated between the jaws 3 and 4.

In this way, according to this embodiment, the pair of jaws 3 and 4 are opened and closed through selective pulling of the two wires 5a and 5b.

In a case in which a pushing force of a wire is used as a driving force for opening or closing the pair of jaws 3 and 4, the pushing force may not be transmitted to the distal-end section of the wire due to buckling, curvature, etc. at the intermediate position of the wire. Such a reduction in the pushing-force transmission efficiency tends to occur particularly in a treatment tool having a flexible shaft or joint section.

In contrast to this, in a case in which pulling forces of the wires 5a and 5b are used as driving forces for both opening and closing the jaws 3 and 4, the pulling forces are reliably transmitted from the proximal-end sections of the wires 5a and 5b to the distal-end sections thereof. Accordingly, there is an advantage in that it is possible to reliably rotate the jaws 3 and 4 by an angle corresponding to a pulling force applied to the proximal-end section of the wire 5a or 5b, to reliably open or close the jaws 3 and 4.

Furthermore, the gripping mechanism 1 is of the both-opening type, in which the jaws 3 and 4 are both rotated in mutually opposite directions. Therefore, there is an advantage in that a large opening angle between the jaws 3 and 4 can be obtained in the open state.

Furthermore, transmission of a rotational force from the first jaw 3, which is a driving side, to the second jaw 4, which is a driven side, is achieved by the single transmission pin 6 and the slits 7 and 8, which are easily machined. Specifically, there is an advantage in that it is possible to transmit a rotational force between the jaws 3 and 4 with a simple structure having a small number of parts.

Figure 4:
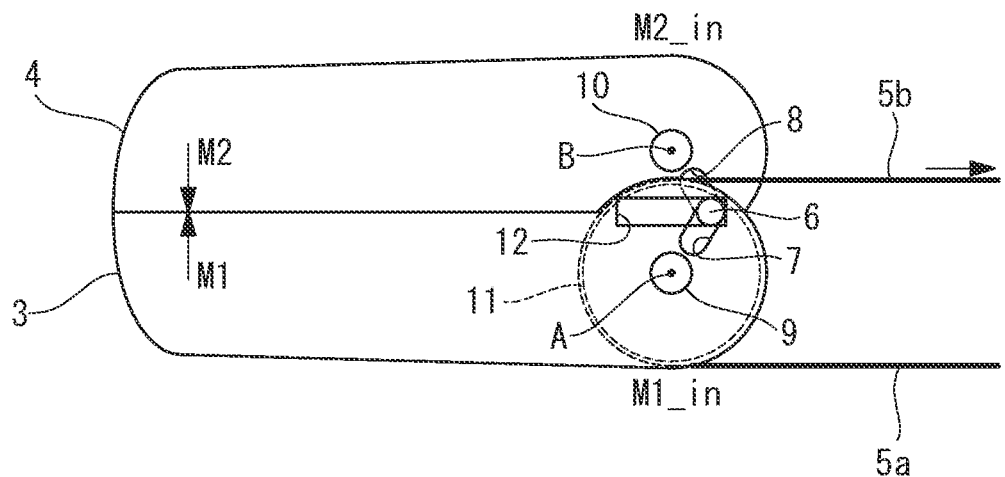
FIG. 4 is a schematic configuration view of a modification of the gripping mechanism shown in FIG. 1A.

As shown in FIG. 4, in this embodiment, a slit (third slit) 12 inside which the transmission pin 6 passes may be formed in the frame 2.

The slit 12 extends in a direction intersecting (in the example shown in the figure, a direction orthogonal to) a straight line connecting the rotation axes A and B and guides, during rotation of the first jaw 3, the transmission pin 6 in the front-back direction along a predetermined movement route. In this way, the movement route of the transmission pin 6 is defined by the slit 12, whereby it is possible to further stabilize the opening and closing operations of the jaws 3 and 4.

Figure 5:
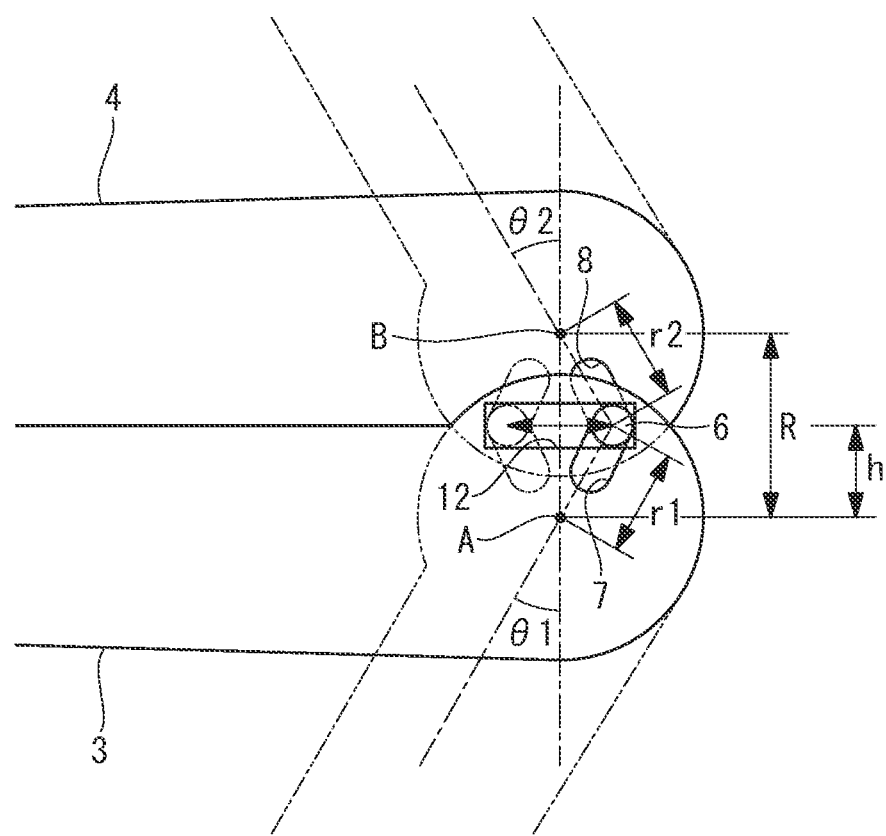
FIG. 5 is a view for explaining the relationship between geometric parameters and a gripping force, in the gripping mechanism shown in FIG. 4.

In a modification shown in FIG. 4, the maximum opening angle of the jaws 3 and 4 is defined by the slit 12 and the lengths of the slits 7 and 8. In FIG. 5, the two-dot chain lines show the maximum open state in which the opening angle between the jaws 3 and 4 is the maximum.

It is preferred that the position of the transmission pin 6 in the closed state and the position of the transmission pin 6 in the maximum open state be approximately symmetric with respect to the straight line connecting the rotation axes A and B. Furthermore, it is preferred that a distance R be 2 to 2.3 times larger than a distance h.

As shown in FIG. 5, the distance R is the distance between the rotation axes A and B. The distance h is the distance between the first rotation axis A of the first jaw 3 and the center of the slit 12 of the frame 2 in the up-down direction. A distance r1 is the distance between the first rotation axis A of the first jaw 3 and the center of the transmission pin 6. A distance r2 is the distance between the second rotation axis B of the second jaw 4 and the center of the transmission pin 6. An opening angle $\theta 1$ is an angle formed by the straight line connecting the rotation axes A and B and a straight line connecting the first rotation axis A and the center of the transmission pin 6. An opening angle $\theta 2$ is an angle formed by the straight line connecting the rotation axes A and B and a straight line connecting the second rotation axis B and the center of the transmission pin 6.

In a case in which the slit 12 is located at the lower side of the center between the rotation axes A and B, the opening angle $\theta 2$ of the second jaw 4 becomes less than the opening angle $\theta 1$ of the first jaw 3. This means that a rotational force transmitted from the first jaw 3 to the second jaw 4 is multiplied through reduction of the speed of rotation, to increase the gripping force between the jaws 3 and 4. Therefore, it is preferred that the slit 12 be formed at the lower side of the center between the rotation axes A and B. On the other hand, in the gripping mechanism 1, which is of the both-opening type, it is preferred that the difference between the opening angles $\theta 1$ and $\theta 2$ be small.

The distance R is set to be 2 to 2.3 times larger than the distance h, whereby the gripping force can be increased while the difference between the opening angles $\theta 1$ and $\theta 2$ is suppressed within an acceptance range.

In a state in which a gripping force is generated between the jaws 3 and 4, a moment $M1\_in$ input to the proximal-end section of the first jaw 3 and a moment $M1$ output from the distal-end section of the first jaw 3 balance each other. Furthermore, a moment $M2\_in$ input to the proximal-end section of the second jaw 4 and a moment $M2$ output from the distal-end section of the second jaw 4 balance each other. In the following expressions, e indicates a multiplication factor of a moment from the first jaw 3 to the second jaw 4.

$M1=M1\_in$ $M2=eM2\_in$

On the other hand, the sum Min of input moments is constant.

$Min=M1\_in + M2\_in$

Accordingly, the sum Min of moments is distributed to the jaws 3 and 4 by the ratio of the multiplication factor e.

$M1\_in:M2\_in=e:1$

Thus, a gripping force Mjaw is expressed by the following expression.

$Mjaw = Min \times e/(1+e) = 1 - Min \times 1/(1+e)$

From the above, it is understood that the gripping force Mjaw is increased as the multiplication factor e of the second jaw 4 becomes larger.

Figure 6A:
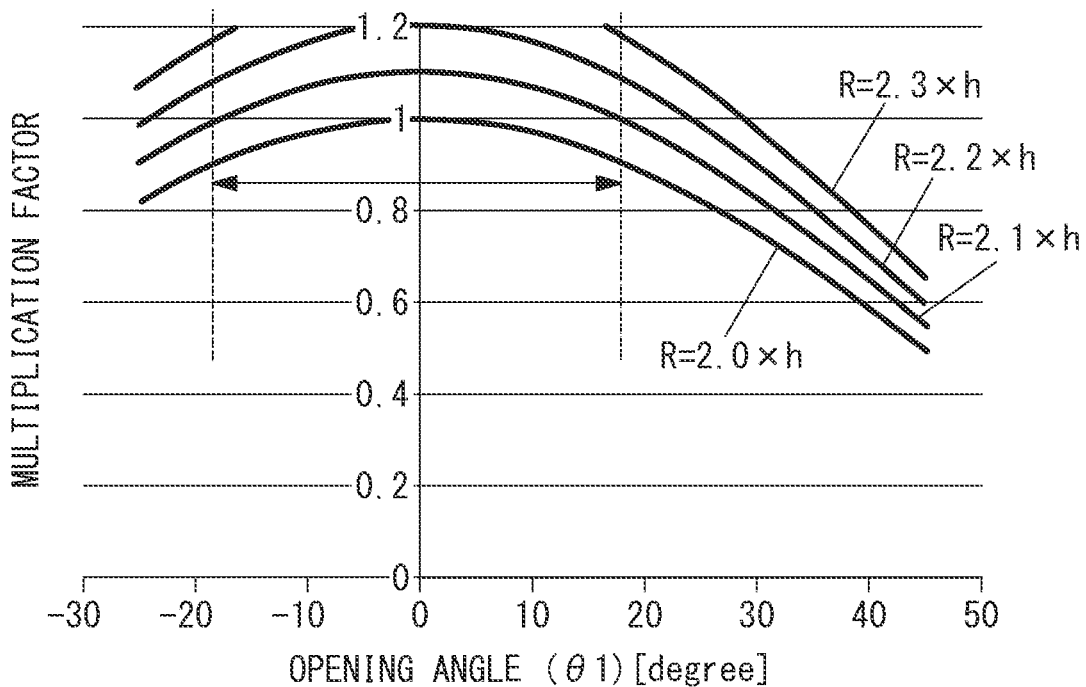
FIG. 6A is a graph representing the relationship between an opening angle θ1 and a force multiplication factor, in the gripping mechanism shown in FIG. 4.

FIG. 6A shows calculation results of the multiplication factor of a rotational force when the distance h is changed with respect to the distance R. As the distance h is reduced, i.e., as the slit 12 is displaced to a lower side, the multiplication factor of the rotational force is increased.

Figure 6B:
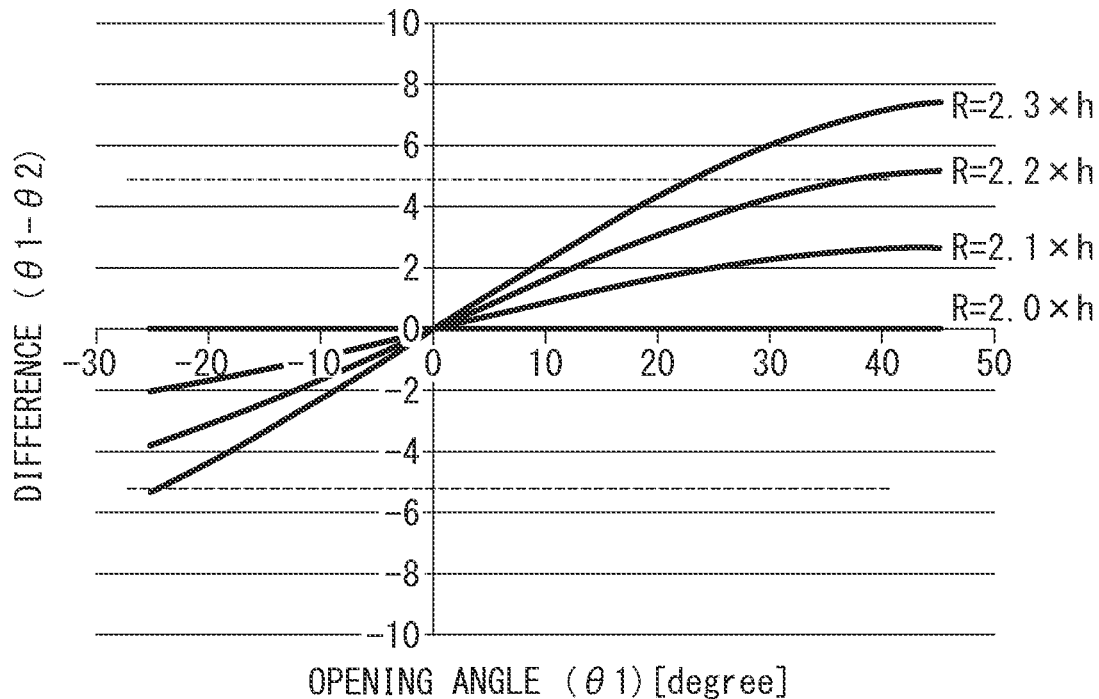
FIG. 6B is a graph representing the relationship between the opening angle θ1 and the difference between opening angles θ1 and θ2, in the gripping mechanism shown in FIG. 4.

FIG. 6B shows the relationship between the opening angle θ1 of the first jaw 3 and the difference (θ1−θ2) between the opening angles θ1 and θ2 of the jaws 3 and 4. The difference (θ1−θ2) of about 20% or less of the opening angle θ1 falls within the acceptance range. In the range where R is 2.3×h or less, the difference (θ1−θ2) is 20% or less of the opening angle θ1.

Note that, in the configuration shown in FIG. 5, the distance r1, the distance r2, the opening angle θ2, and the multiplication factor e are respectively expressed by the following formulae.

$$r1 = \frac{h}{\cos\theta 1}$$

$$r2 = \sqrt{(R-h)^2 + (h \times \tan\theta 1)^2}$$

$$\tan\theta 2 = \frac{h \times \tan\theta 1}{R - h}$$

$$e = \frac{r2}{r1}\cos\theta 1 \cos\theta 2$$

Figure 7A:
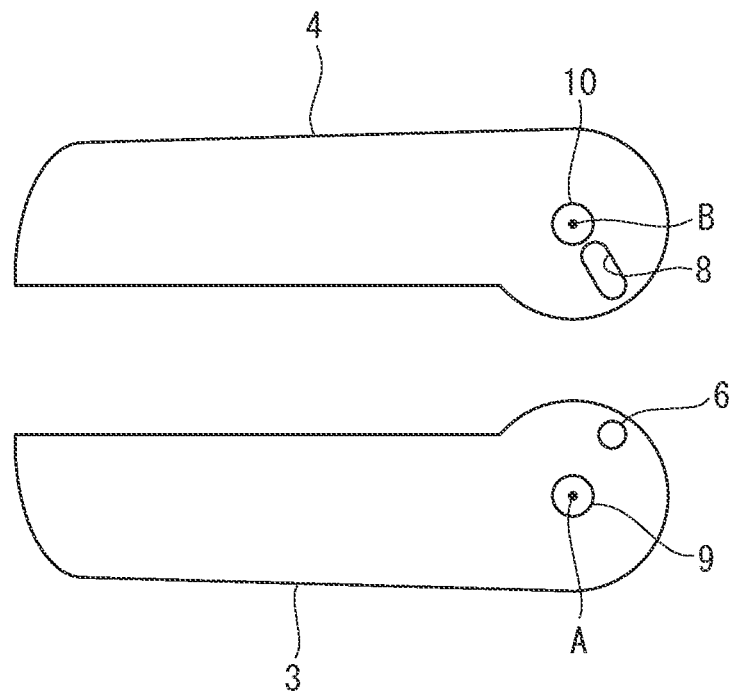
FIG. 7A is a schematic exploded view of a modification of the gripping mechanism shown in FIG. 1A.
Figure 7B:
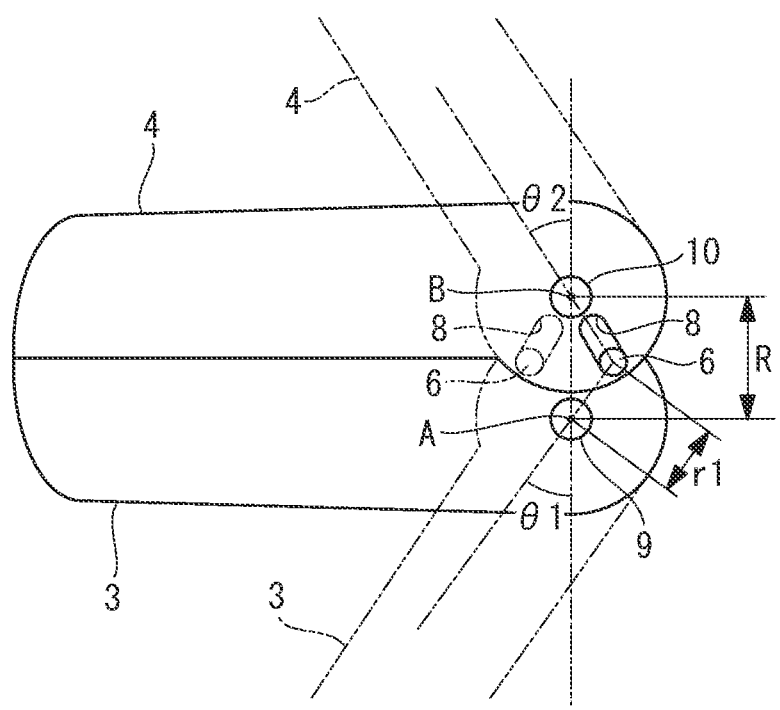
FIG. 7B is a schematic configuration view of a gripping mechanism shown in FIG. 7A.

In this embodiment, as shown in FIGS. 7A and 7B, it is also possible to attach the transmission pin 6 to one of the pair of jaws 3 and 4 and to form a slit in only the other one of the pair of jaws 3 and 4. In the example shown in FIGS. 7A and 7B, the transmission pin 6 is attached to the first jaw 3, and the slit 8 is formed in the second jaw 4.

In this way, the transmission pin 6 is formed integrally with the jaw 3, whereby the number of parts can be further reduced. Furthermore, because the contact area of the transmission pin 6 with an inner surface of the slit is reduced, loss of a force due to the friction can be reduced.

In the configuration of FIGS. 7A and 7B, it is preferred that the distance R be 2 to 2.2 times larger than the distance r1. The ratio of the distance R and the distance r1 falls within the above-described range, whereby a rotational force transmitted to the second jaw 4 can be multiplied to increase the gripping force, while the difference between the opening angles θ1 and θ2 is suppressed within the acceptance range.

Figure 8A:
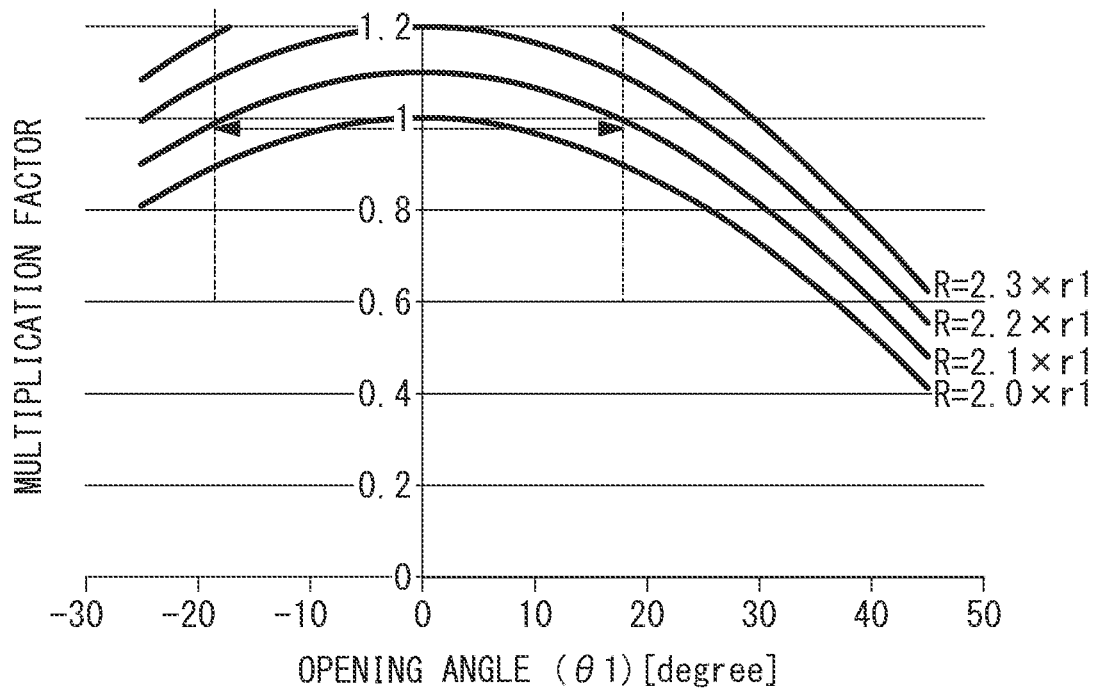
FIG. 8A is a graph representing the relationship between the opening angle θ1 and a force multiplication factor, in the gripping mechanism shown in FIG. 7B.
Figure 8B:
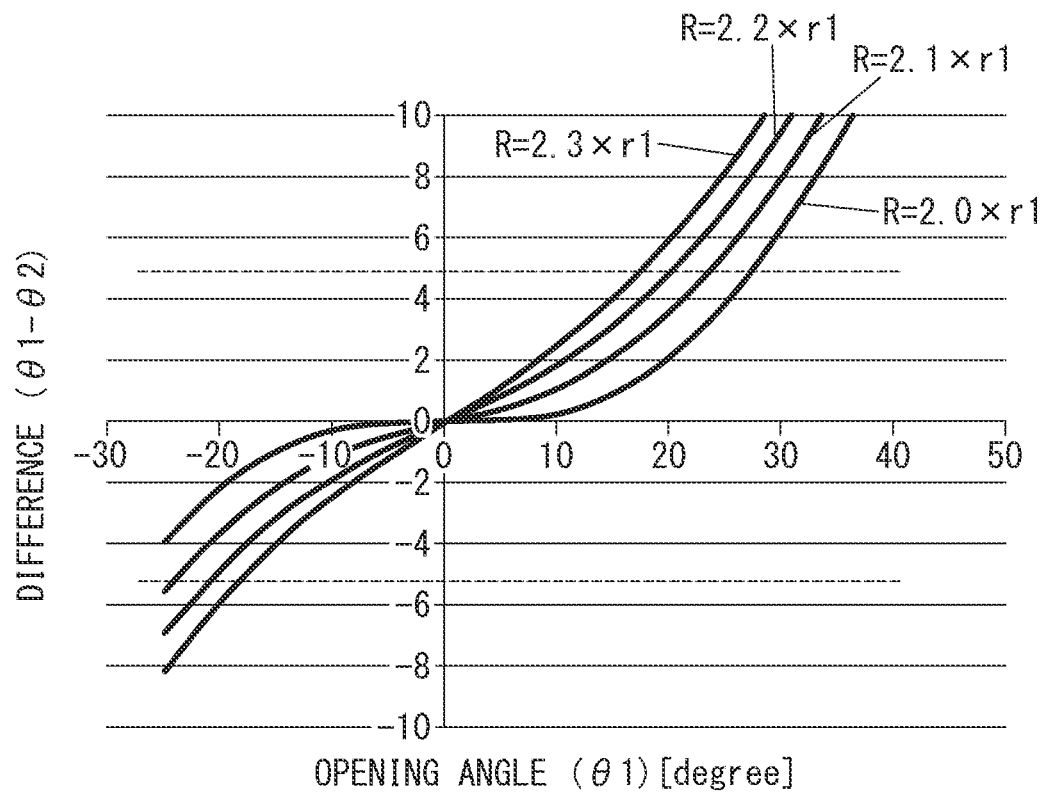
FIG. 8B is a graph representing the relationship between the opening angle θ1 and the difference between the opening angles θ1 and θ2, in the gripping mechanism shown in FIG. 7B.

FIG. 8A shows the relationship between the opening angle θ1 and the multiplication factor e in the configuration shown in FIGS. 7A and 7B. FIG. 8B shows the relationship between the opening angle θ1 and the difference (θ1−θ2) in the configuration shown in FIGS. 7A and 7B.

Note that, in the configuration shown in FIGS. 7A and 7B, the distance r2, the opening angle θ2, and the multiplication factor e are respectively expressed by the following formulae.

$$r2 = \sqrt{(R - r1 \times \cos\theta 1)^2 + (r1 \times \sin\theta 1)^2}$$

$$\tan\theta 2 = \frac{r1 \times \sin\theta 1}{R - r1 \times \cos\theta 1}$$

$$e = \frac{r2}{r1}\cos(\theta 1 + \theta 2)$$

Figure 9A:
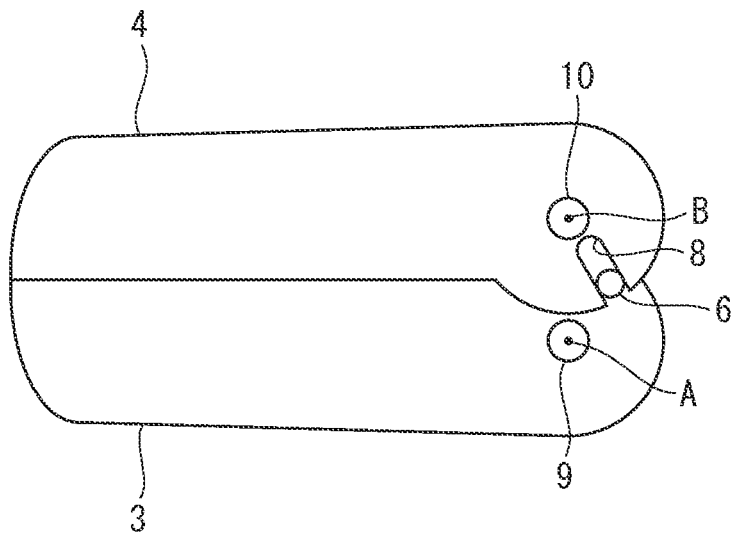
FIG. 9A is a schematic view showing a modification of a slit in a second jaw of the gripping mechanism shown in FIG. 7B.
Figure 9B:
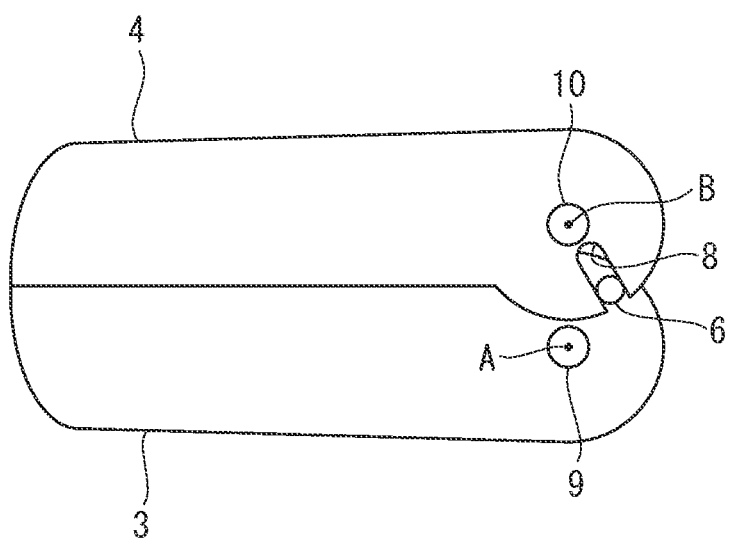
FIG. 9B is a schematic view showing another modification of the slit in the second jaw of the gripping mechanism shown in FIG. 7B.

In the configuration in which the transmission pin 6 is formed integrally with the first jaw 3, as shown in FIGS. 9A and 9B, one end of the slit 8 may be open at the outer circumferential surface of the second jaw 4. The slit 8 that is shown in FIG. 9A is formed from an inner surface of the second jaw 4 to an intermediate position thereof in the left-right direction. The slit 8 that is shown in FIG. 9B penetrates the second jaw 4 in the left-right direction.

At the time of assembly of the jaws 3 and 4, the transmission pin 6 is inserted into the slit 8 from the opening in the outer circumferential surface of the second jaw 4, whereby the jaws 3 and 4 can be easily assembled.

Figure 10A:
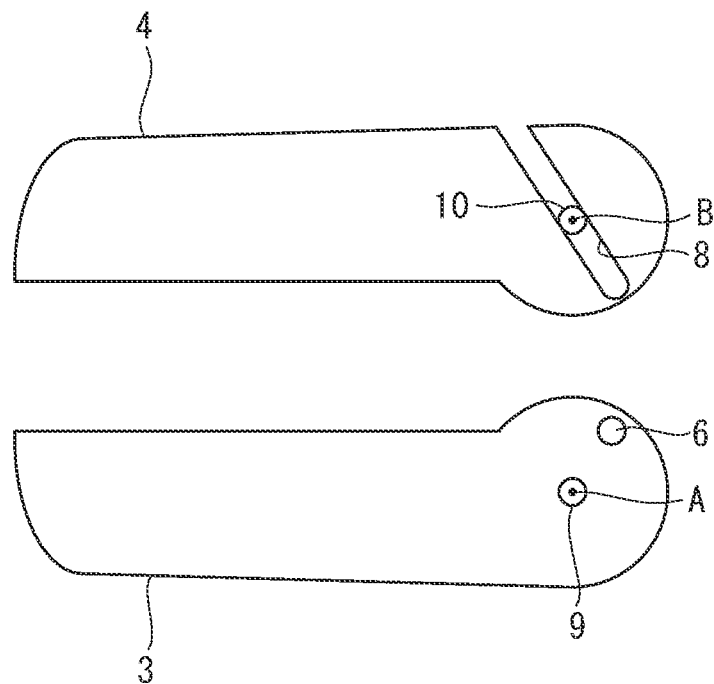
FIG. 10A is a schematic view showing another modification of the slit in the second jaw of the gripping mechanism shown in FIG. 7B.
Figure 10B:
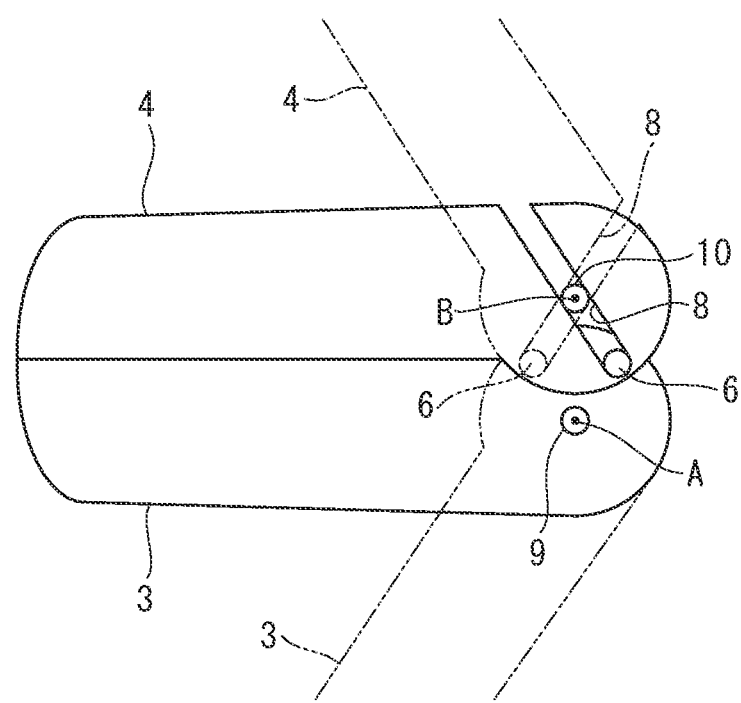
FIG. 10B is a schematic configuration view of a gripping mechanism that includes the second jaw shown in FIG. 10A.

As shown in FIGS. 10A and 10B, the slit 8 may extend from the position of the transmission pin 6 when in the closed state of the jaws 3 and 4 to the outer circumferential surface of the second jaw 4 by passing through the second rotation axis B, whereby one end of the slit 8 is open at the outer circumferential surface of the second jaw 4. The slit 8 may be straight in shape as shown in FIGS. 10A and 10B or may be curved or bent between the second rotation axis B and the opening in the outer circumferential surface.

In the assembly process of the jaws 3 and 4, after the transmission pin 6 is inserted into the slit 8, the connecting pin 10 is inserted into the slit 8. Therefore, the transmission pin 6 can be prevented from getting out from the slit 8 by the connecting pin 10. Furthermore, because the connecting pin 10 restricts the range of opening and closing operations of the jaws 3 and 4, the opening and closing operations of the jaws 3 and 4 do not become unstable.

Figure 11:
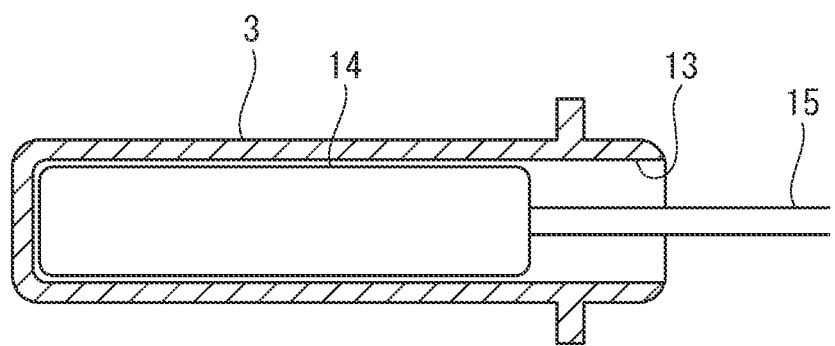
FIG. 11 is a schematic view showing an internal configuration of a modification of a first jaw of the gripping mechanism shown in FIG. 7B.

In the configuration in which the transmission pin 6 is formed integrally with the first jaw 3, as shown in FIG. 11, it is possible to form, inside the first jaw 3, a hollow 13 that continues in the longitudinal direction from the distal-end section of the first jaw 3 to a proximal-end surface thereof. The hollow 13 can be used as a wiring route, to impart various functions to the first jaw 3.

For example, in a case in which the first jaw 3 is imparted a function as an energy treatment device, a cable 15 for supplying an energy source to an energy treatment part 14 in the first jaw 3 is wired in the hollow 13. When the energy source is supplied, the energy treatment part 14 releases energy, such as heat, ultrasound, or high-frequency current.

In a case in which the first jaw 3 is imparted is imparted a function for measuring a gripping force or tissue hardness, a contact sensor is mounted on the first jaw 3, and a cable for the contact sensor is wired in the hollow 13.

Figure 12A:
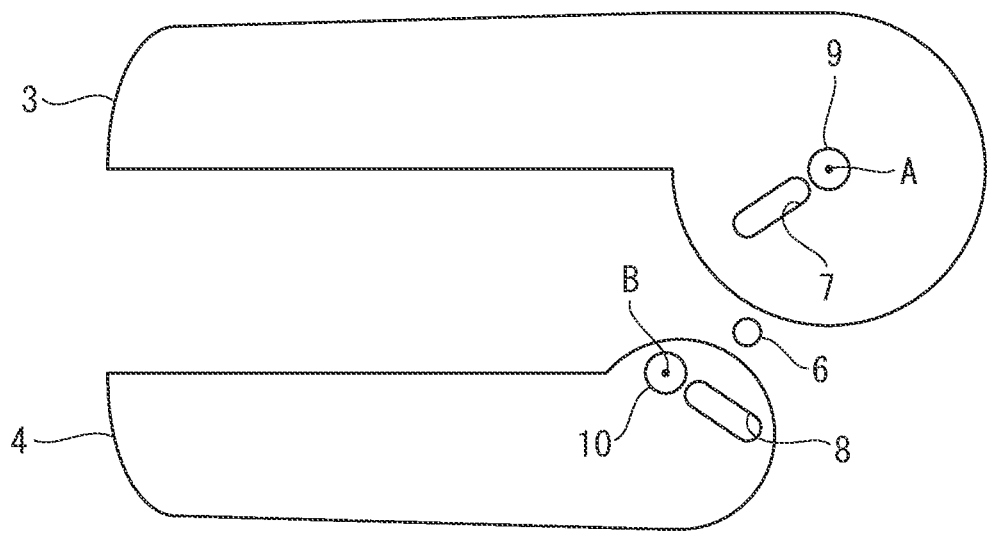
FIG. 12A is a schematic exploded view of another modification of the gripping mechanism shown in FIG. 1A.
Figure 12B:
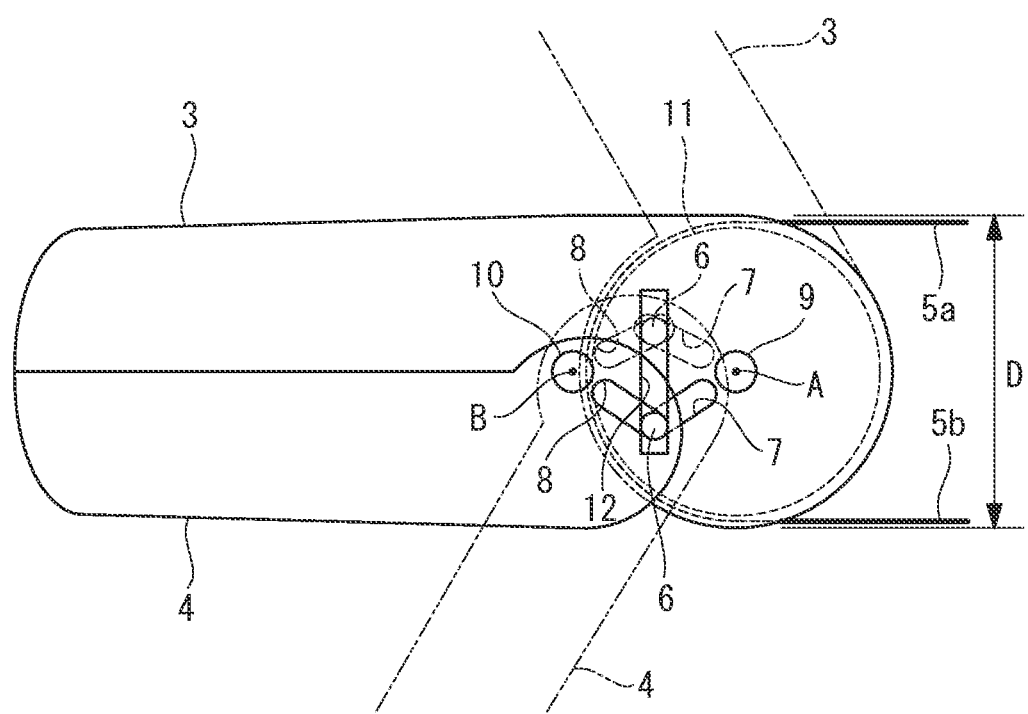
FIG. 12B is a schematic configuration view showing a closed state of the gripping mechanism shown in FIG. 12A.

In this embodiment, although the rotation axes A and B are disposed in parallel in the up-down direction, instead of this, as shown in FIGS. 12A and 12B, the rotation axes A and B may be disposed one behind another in the front-back direction. In FIGS. 12A and 12B, an upper jaw is the driving-side first jaw 3 and a lower jaw is the driven-side second jaw 4. It is preferred that the rotation axis B of the second jaw 4 be disposed at a position closer to the distal end than the rotation axis A of the first jaw 3 is.

By arranging the rotation axes A and B in the front-back direction, the diameter of the gripping mechanism 1 can be reduced in the up-down direction. Furthermore, compared with the configuration in which the rotation axes A and B are arranged in the up-down direction, it is possible to increase the outer diameter of the guide surface 11, which is used for driving, to increase the gripping force.

In the state in which the jaws 3 and 4 are closed, it is preferred that the first rotation axis A be positioned at the center of an outer diameter D of the jaws 3 and 4. The outer diameter D of the jaws 3 and 4 is a dimension from an upper surface of the first jaw 3 to a lower surface of the second jaw 4 in the closed state of the jaws 3 and 4. According to this configuration, the outer diameter of the guide surface 11 is set to be approximately equal to the outer diameter D of the gripping mechanism 1, whereby a driving force (rotational force) given from the wire 5 to the first jaw 3 can be maximized in a range in which the outer diameter D is not increased.

Figure 13A:
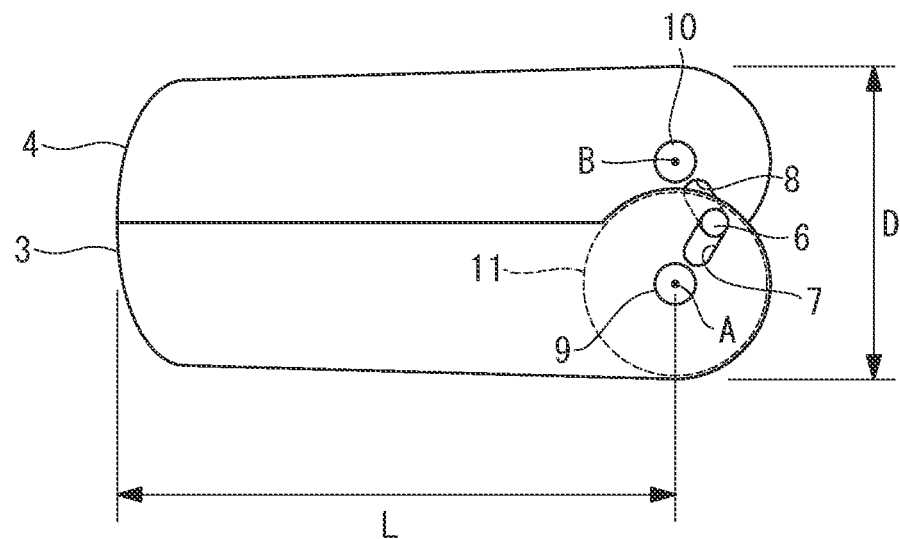
FIG. 13A is a view for explaining a gripping force of a gripping mechanism in which the first rotation axis and the second rotation axis are disposed in parallel.
Figure 13B:
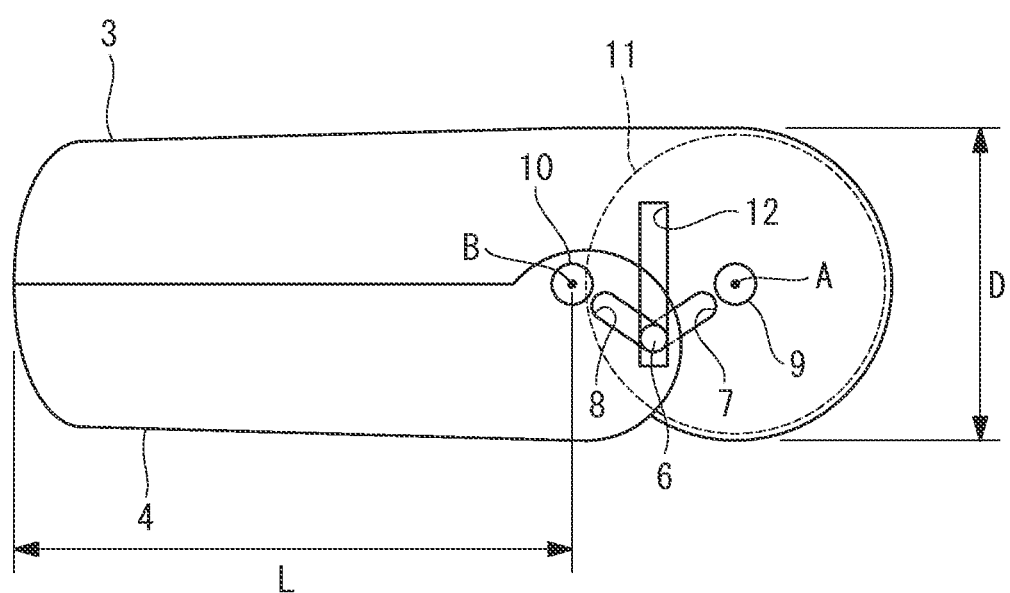
FIG. 13B is a view for explaining a gripping force of a gripping mechanism in which the first rotation axis and the second rotation axis are disposed one behind another.

FIGS. 13A and 13B show a comparison of the magnitudes of gripping forces between a case in which the rotation axes A and B are disposed in parallel and a case in which the rotation axes A and B are disposed one behind another.

In the case of FIG. 13A, in which the rotation axes A and B are disposed in parallel, the radius of the guide surface 11 is designed to be equal to or less than ⅓ of the outer diameter D of the gripping mechanism 1. In this case, a gripping force Fp is expressed by the following Formula (1).

In the case of FIG. 13B, in which the rotation axes A and B are disposed one behind another, the radius of the guide surface 11 is designed to be equal to or less than ½ of the outer diameter D. In this case, a gripping force Fs is expressed by the following Formula (2).

In Formulae (1) and (2), L indicates the length from the distal end of the first jaw 3 to the rotation axis A. Fin indicates a rotational force input from the wire 5a to the transmission pin 6.

$$Fp = \frac{D}{3L} \cdot \frac{e}{1+e} \cdot Fin \qquad (1)$$

$$Fs = \frac{D}{2} \cdot \frac{e}{L+e(L+R)} \cdot Fin \qquad (2)$$

In order that the gripping force Fs is larger than the gripping force Fp (Fs>Fp), the length L and the distance R need satisfy the following Formula (3).

$$L > 2e/(1+e) \times R \qquad (3)$$

In the case of the configuration in which the three slits 7, 8, and 12 are provided, L>1.13R is satisfied. In the case of the configuration in which the transmission pin 6 is formed integrally with the jaw 3, L>1.09R is satisfied. Specifically, in various configurations having the slits 7, 8, and 12 and the transmission pin 6, Formula (3) is satisfied. Thus, the gripping force can be increased by disposing the rotation axes A and B one behind another.

Figure 14:
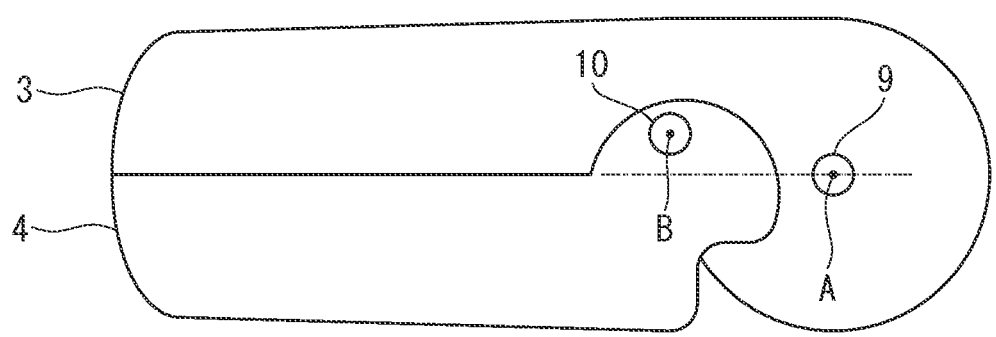
FIG. 14 is a schematic view showing a modification of the second rotation axis of the gripping mechanism shown in FIG. 12A.

In the configuration in which the rotation axes A and B are disposed one behind another, as shown in FIG. 14, the rotation axis B of the second jaw 4 may be located at the first jaw 3 side (upper side) of the center (see the one-dot chain line) of the outer diameter D of the gripping mechanism 1.

Figure 15A:
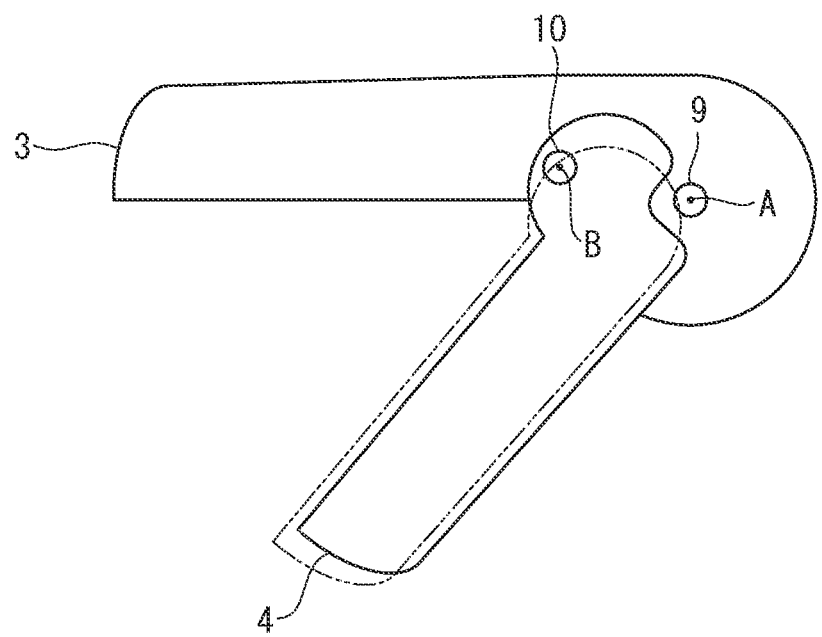
FIG. 15A is a schematic view for explaining an opening angle of the second jaw when the second rotation axis is located at a position closer to the first jaw than the center of the outer diameter is.
Figure 15B:
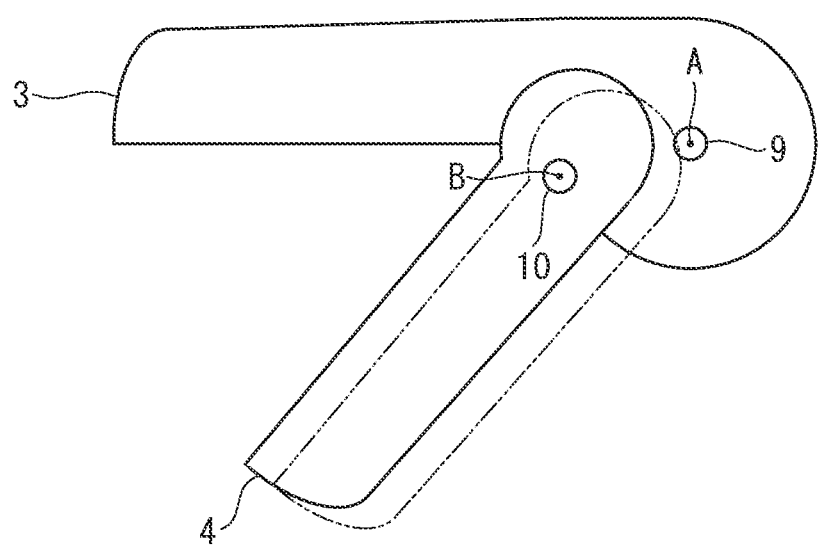
FIG. 15B is a schematic view for explaining an opening angle of the second jaw when the second rotation axis is located at a position closer to the second jaw than the center of the outer diameter is.

FIGS. 15A and 15B explain the relationship between the position of the second rotation axis B and the opening angle of the second jaw 4. In FIGS. 15A and 15B, the two-dot chain line shows the position of the second jaw 4 when the second rotation axis B is located at the center of the outer diameter D.

As shown in FIG. 15A, in a case in which the second rotation axis B is located at an upper side of the center of the outer diameter D, in the open state, the second jaw 4 is offset to a lower side of the position indicated by the two-dot chain line. On the other hand, as shown in FIG. 15B, in a case in which the second rotation axis B is located at a lower side of the center of the outer diameter D, in the open state, the second jaw 4 is offset to an upper side of the position indicated by the two-dot chain line.

In this way, the second rotation axis B is disposed at an upper side (the first jaw 3 side) of the center of the outer diameter D, whereby it is possible to widen the opening width between the jaws 3 and 4 in the up-down direction and to more easily grip a gripping target, such as living tissue, by using the jaws 3 and 4.

REFERENCE SIGNS LIST

1 gripping mechanism
2 frame
3 first jaw
4 second jaw
5, 5a, 5b wire
6 transmission pin
7 slit (first slit)
8 slit (second slit)
9, 10 connecting pin
11 guide surface
12 slit (third slit)
A first rotation axis
B second rotation axis

The invention claimed is:

1. A gripping mechanism comprising:
a frame;
a first jaw and a second jaw each supported by the frame so as to be configured to be opened and closed relative to each other;
a slit formed in at least one of the first jaw and the second jaw;
a transmission pin that passes inside the slit and that transmits a force between the first jaw and the second jaw; and
a wire connected to the first jaw,
wherein a proximal-end section of the first jaw is supported by the frame so as to be rotatable about a first rotation axis,
a proximal-end section of the second jaw is supported by the frame so as to be rotatable about a second rotation axis different from the first rotation axis and parallel to the first rotation axis,
the wire gives a rotational force about the first rotation axis to the first jaw through tension,
the transmission pin moves inside the slit through rotation of the first jaw about the first rotation axis, and the second jaw is rotated about the second rotation axis through the movement of the transmission pin inside the slit,
the slit comprises a first slit formed in the first jaw, a second slit formed in the second jaw, and a third slit formed at a position of the frame between the first rotation axis and the second rotation axis,
the transmission pin passes inside the first slit, the second slit, and the third slit, and
the transmission pin moves inside the first slit, the second slit, and the third slit through rotation of the first jaw about the first rotation axis.

2. The gripping mechanism according to claim 1, wherein a position of the transmission pin in a state in which the first jaw and the second jaw are closed and a position of the transmission pin in a state in which the first jaw and the second jaw are opened at the maximum opening angle are approximately symmetric with respect to a straight line connecting the first rotation axis and the second rotation axis.

3. The gripping mechanism according to claim 2, wherein a distance between the first rotation axis and the second rotation axis is 2 to 2.3 times larger than a distance between the first rotation axis and the third slit.

4. The gripping mechanism according to claim 1, wherein the first rotation axis is located at a center of an outer diameter of the first and second jaws in a closed state.

5. The gripping mechanism according to claim 4, wherein the second rotation axis is located at a position closer to a distal end than the first rotation axis is and closer to the first jaw than the center of the outer diameter is.

6. A gripping mechanism according to:
a frame;
a first jaw and a second jaw each supported by the frame so as to be configured to be opened and closed relative to each other;
a slit formed in at least one of the first jaw and the second jaw;
a transmission pin that passes inside the slit and that transmits a force between the first jaw and the second jaw; and
a wire connected to the first jaw,
wherein a proximal-end section of the first jaw is supported by the frame so as to be rotatable about a first rotation axis,
a proximal-end section of the second jaw is supported by the frame so as to be rotatable about a second rotation axis different from the first rotation axis and parallel to the first rotation axis,
the wire gives a rotational force about the first rotation axis to the first jaw through tension,
the transmission pin moves inside the slit through rotation of the first jaw about the first rotation axis, and the second jaw is rotated about the second rotation axis through the movement of the transmission pin inside the slit,
the transmission pin is attached to one of the first jaw and the second jaw,
the slit is formed in the other one of the first jaw and the second jaw, and
wherein a position of the transmission pin in a state in which the first jaw and the second jaw are closed and a position of the transmission pin in a state in which the first jaw and the second jaw are opened at the maximum opening angle are approximately symmetric with respect to a straight line connecting the first rotation axis and the second rotation axis.

7. The gripping mechanism according to claim 6, wherein a distance between the first rotation axis and the second rotation axis is 2 to 2.2 times larger than a distance between the transmission pin and the rotation axis of the one of the first jaw and the second jaw to which the transmission pin has been attached.

8. A gripping mechanism according to comprising:
a frame;
a first jaw and a second jaw each supported by the frame so as to be configured to be opened and closed relative to each other;
a slit formed in at least one of the first jaw and the second jaw;
a transmission pin that passes inside the slit and that transmits a force between the first jaw and the second jaw; and
a wire connected to the first jaw,
wherein a proximal-end section of the first jaw is supported by the frame so as to be rotatable about a first rotation axis,
a proximal-end section of the second jaw is supported by the frame so as to be rotatable about a second rotation axis different from the first rotation axis and parallel to the first rotation axis,
the wire gives a rotational force about the first rotation axis to the first jaw through tension,
the transmission pin moves inside the slit through rotation of the first jaw about the first rotation axis, and the second jaw is rotated about the second rotation axis through the movement of the transmission pin inside the slit,
the transmission pin is attached to one of the first jaw and the second jaw,
the slit is formed in the other one of the first jaw and the second jaw, and
one end of the slit is open at an outer circumferential surface of the other one of the first jaw and the second jaw.

9. The gripping mechanism according to claim 8, wherein the slit extends from a position of the transmission pin in a state in which the first jaw and the second jaw are closed at the outer circumferential surface of the other one of the first jaw and the second jaw, beyond the rotation axis of the other one of the first jaw and the second jaw.

* * * * *